United States Patent [19]
Burrell et al.

[11] Patent Number: 5,365,016
[45] Date of Patent: Nov. 15, 1994

[54] MODIFICATION OF STARCH PRODUCTION

[75] Inventors: Michael M. Burrell, Cottenham; Stephen A. Coates, Cherry Hinton, both of England

[73] Assignee: Advanced Technologies (Cambridge) Limited, Cambridge, United Kingdom

[21] Appl. No.: 893,315

[22] Filed: Jun. 3, 1992

[30] Foreign Application Priority Data

Jun. 12, 1991 [GB] United Kingdom ............... 9112645

[51] Int. Cl.$^5$ ....................... A01H 5/00; C12N 15/00; C07H 21/04
[52] U.S. Cl. ................................. 800/205; 800/255; 800/DIG. 42; 435/172.3; 435/320.1; 536/24.5
[58] Field of Search ............... 800/205, 250, DIG. 42, 800/255; 435/172.3, 320.1; 536/24.5

[56] References Cited

FOREIGN PATENT DOCUMENTS 0240208 10/1987 European Pat. Off. .
9211376 7/1992 Sweden .

OTHER PUBLICATIONS

Visser, R., et al. Mol. Gen. Genet., vol. 225 (1991) pp. 289–296.
Klösgen, R., et al. Mol. Gen. Genet, vol. 203 (1986) pp. 237–244.
Horsch, R., et al. Science, vol. 223 (1984) pp. 496–498.
Wang, Z-y., et al Nucl. Acids Res., vol. 18, (1991) pp. 5898.
Blundy, K., et al. Plant Mol. Biol., vol. 16 (1991) pp. 153–160.
D. Mares, et al., Ch. 9, Pozato Physiology (1985) Academic Press, Inc., see p. 297.
Hovenkamp Hernelink, J., et al. Theor. Appl. Genet., vol. 75 (1987) pp.217–221.
Euphytica 59:83–91.
Gene 98 (1991) 243–248.
Molecular Strategies for Crop Improvement p. 271.
Cell vol. 35. 225–233 Nov. 1983.
Plant Molecular Biology 16:1099–1101. 1991.
Gene 72(1988) 45–50.

*Primary Examiner*—David T. Fox
*Assistant Examiner*—Charles Rories
*Attorney, Agent, or Firm*—Kane, Dalsimer, Sullivan, Kurucz, Levy, Eisele and Richard

[57] ABSTRACT

A process is provided whereby the constitution of starch produced in a plant is altered without there being a substantial change in the total amount of starch which is produced. In the process a plant cell is transformed using a chimaeric gene comprising an antisense coding sequence from the waxy locus of a plant genome or an antisense similar coding sequence from a non-plant genome.

11 Claims, 1 Drawing Sheet

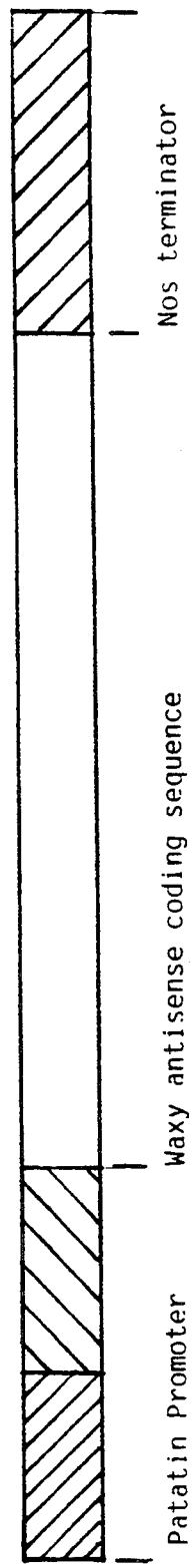

MODIFICATION OF STARCH PRODUCTION

BACKGROUND OF THE INVENTION

1. Field of the Invention

The subject invention relates to the process of starch production in plants.

2. Brief Description of the Related Art

It is an object of the invention to effect a change in the nature of the starch produced in a plant without reducing, or without substantially reducing, the amount of starch which the plant produces. Starch is used in the food, chemical, paper and textile industries. In these industries the nature of a starch affects its suitability for use in a particular process.

It has been reported that potato plants have been transformed to produce antisense RNA from a gene construct containing starch synthase cDNA in reverse orientation, and that this gave rise to tubers containing amylose-free starch. See "Inhibition of the expression of the gene for granule-bound starch synthase in potato by antisense constructs", R. G. F. Visser et al, Mol. Gen. Genet. (1991) 225: 289-296.

In the mutant form of maize known as waxy maize the process for producing amylose is suppressed and thereby the total amount of starch which is produced is less than is the case with maize not embodying the waxy gene.

SUMMARY OF THE INVENTION

The subject invention provides a process for altering starch production in a plant, which process comprises transforming a plant cell with a chimaeric gene comprising a promoter and an antisense coding sequence from the waxy locus of a plant genome or an antisense similar coding sequence from a non-plant genome.

BRIEF DESCRIPTION OF THE DRAWINGS

The drawing shows diagrammatically an anti-sense chimaeric gene used in the process of the invention.

DETAILED DESCRIPTION OF THE PREFERRED EMBODIMENTS OF THE INVENTION

The plant the subject of the inventive process is suitably a plant from which starch is commercially derived; e.g. potato, rice, wheat, barley or maize.

The genome from which the coding sequence is derived may be, for example, that of a wheat plant or a maize plant.

By "coding sequence from the waxy locus" is meant an unmutated sequence, not a sequence of or from the mutant waxy gene. The sequence can be the whole sequence or an operable part or parts thereof.

It is a result of carrying out the subject invention that the enzymic activity of starch synthase is reduced. This being the case, it would have been expected that the total amount of starch would have been reduced. Surprisingly though, there is no apparent reduction in the total amount of starch when the invention is carried into effect.

The promoter should be such as to cause the reduction in starch synthase activity to be effected at the main starch location of the plant, this being, for example, in the tubers for potato and in the seeds for wheat or rice.

An example of the inventive process will now be given.

The waxy coding sequence was obtained from a cDNA library of wheat endosperm RNA. The sequence, in sense orientation, as described by Clark et al (Plant Molecular Biology 16, 1099-101, 1991. The waxy coding sequence was blunt end ligated into the plasmid pFW4101 in place of the GUS (B-glucuronidase) coding sequence to produce the antisense chimaeric gene (see the drawing accompanying herewith) in plasmid pFW4082. pFW4101 was constructed with a patatin promoter made from two genomic clones PS3 and PS27 as described by Blundy et al (Plant Molecular Biology 16, 153–160, 1991). The patatin fragments PS3 and PS27 were derived from the genomic clones described by Mignery et al (Gene 62, 27–44, 1988). The fragments consist of −3.5 kb to −1 kb of PS3 and −1 kb to +3 of PS27 numbered in relation to the translation start. pFW4101 was also provided with a Nos terminator sequence.

*E. coli* harbouring pFW4101 and *Agrobacterium tumafaciens* harbouring pFW4082 were deposited under the Budapest Treaty on the International Recognition of the Deposit of Micro-organisms for the Patent Procedure, at the National Collection of Industrial and Marine Bacteria, Aberdeen, GB on 5th Jul. 1990 under accession number NCIMB 40306 and on 6th Jun., 1991 under accession number NCIMB 40422 respectively.

The vector pFW4082 was transferred into *Agrobacterium tumefaciens* strains LBA 4404 and C58#3 by triparental mating. The Agrobacterium strains were used to transform the potato cultivar Desirée. A large family of over 60 transgenic plants were produced and microtubers were produced from them in vitro.

Starch synthase was assayed by making extracts of microtubers and measuring the incorporation of [$^{14}$C] from [$^{14}$C] ADPglucose into starch (methanol insoluble material) by these extracts. This assay revealed that starch synthase activity had been reduced by about 50% as compared with non-transformed plants.

To assess the starch content of the microtubers starch was first extracted from the microtubers with perchloric acid. The extracted starch was then enzymatically converted to glucose which was subsequently assayed spectophotometrically. To assess the accuracy of these measurements, control experiments were performed by taking replicate samples of the extracts to which known amounts of starch were added before starting the assay procedure.

The results showed that when starch synthase activity was reduced by 50%, the starch content of the microtubers remained constant.

In order to measure the amylose content of the starch in the transformed plants the proportion of straight chain glucan in the starch was determined by digesting the starch with exo-amylase. The glucan released was assayed spectrophotometrically and it was thereby determined that the proportion of glucan had been reduced from 60% to 30% and thus that the ratio of amylose to amylopectin was lower in the transformed plants than is the case for non-transformed plants.

As will be appreciated by those skilled in the art, whereas in the above described procedure of transforming potato use was made of *A. tumefaciens*. In applying the subject inventive process in respect of other plants, maize, rice, wheat or barley for example, use may be made of other modes of transformation. Thus, for instance, direct transformation or electroporation may be employed.

We claim:

1. A process for altering starch production in a potato plant, which process comprises transforming a cell of said potato plant with a chimaeric gene comprising a promoter and the antisense coding sequence of waxy locus of a wheat plant genome.

2. A process as claimed in claim 1, wherein a potato plant is regenerated from the transformed cell.

3. A transgenic potato plant prepared by the process of claim 1.

4. A tuber of a transgenic potato plant prepared by the process of claim 1.

5. A seed of a transgenic potato plant prepared by the process of claim 1.

6. A process as claimed in claim 1 wherein said cell is transformed with the plasmid pFW4082.

7. A transgenic starch-producing potato plant derived from a host starch-producing potato plant, which comprises;

a host starch-producing potato plant having a plant cell genome integrated with a chimaeric gene which comprises, in the direction of transcription, the following operably linked components:
- (a) a promoter which functions in the cell to cause a reduction of starch synthase activity in tubers and seeds;
- (b) the antisense coding sequence of the waxy locus of a wheat plant; and
- (c) a terminator sequence which is functional in the cell;

said transgenic plant exhibiting in comparison to the host potato plant from which it is derived
- (i) reduced starch synthase activity; and
- (ii) no apparent reduction in the total amount of starch produced.

8. The transgenic plant of claim 7 wherein the antisense chimaeric gene is the plasmid pFW4082.

9. A tuber of the transgenic plant of claim 7.

10. A seed of the transgenic plant of claim 7.

11. A transgenic potato plant which comprises;

a host potato plant having integrated in a cell thereof a chimaeric which comprises in the direction of transcription, the following operably linked components:
- (a) a promoter which functions in the cell;
- (b) the antisense coding sequence having the unmutated nucleotide sequence of the waxy locus of wheat and
- (c) a terminator sequence which is functional in the cell;

said chimaeric gene being operative to cause a reduction of starch synthase activity in the tuber of said plant; and said transgenic potato plant exhibiting in comparison to the host potato plant from which it is derived
- (i) reduced starch synthase activity; and
- (ii) no apparent reduction in the total amount of starch produced.

* * * * *